United States Patent [19]

Beaumont et al.

[11] Patent Number: 5,527,771
[45] Date of Patent: Jun. 18, 1996

[54] METHODS AND COMPOSITIONS FOR TREATMENT OF DIABETES MELLITUS, HYPOGLYCEMIA & OTHER CONDITIONS

[75] Inventors: Kevin Beaumont; Andrew A. Young, both of San Diego, Calif.

[73] Assignee: Amylin Pharmaceuticals, Inc., San Diego, Calif.

[21] Appl. No.: 260,493

[22] Filed: Jun. 14, 1994

Related U.S. Application Data

[60] Continuation of Ser. No. 129,569, Sep. 29, 1993, abandoned, which is a division of Ser. No. 774,411, Oct. 10, 1991, Pat. No. 5,321,008, which is a continuation-in-part of Ser. No. 670,231, Mar. 15, 1991, Pat. No. 5,264,372, which is a continuation-in-part of Ser. No. 640,478, Jan. 10, 1991, Pat. No. 5,234,906, which is a continuation-in-part of Ser. No. 704,995, May 24, 1991, abandoned.

[51] Int. Cl.⁶ .................... A61K 38/00; A61K 38/23; C07K 14/585; C07K 14/605
[52] U.S. Cl. .................... 514/12; 530/307; 530/308
[58] Field of Search .................... 514/12; 530/307, 530/308

[56] References Cited

FOREIGN PATENT DOCUMENTS 0309100  3/1989  European Pat. Off. .

OTHER PUBLICATIONS

Fertilo et al. Farmaco (Prat) vol. 37 (7) pp. 239–244 (1982).
Zamrazil et al Horm. Metab. Res. 13(1981) pp. 631–635.
Azria et al., "Calcitonins–Physiological and Pharmacological Aspects,"pp. 1–34, Springer–Verlag (1989).
BioWorld Today, vol. 2., No. 125 (1991).
Evans et al., Lancet 1:280 (1978) (cited in the application on p. 23).
Passariello et al., J. Clinical Endocrinology and Metabolism, 53:318–23 (1981) (cited in the application on p. 23).
Blahos et al., Endokinologie, Band 68, Heft 2, 226–30 (1976).
Gattereau et al., J. Clinical Endocrinology and Metabolism 51:354–57 (1980).
Giugliano, Biomedicine & Pharmacotherapy 38:273–77 (1984).
Giugliano et al., Am. J. Physiol. 242:E206–13 (1982).
Giugliano et al., Diabete & Metabolisme 8:213–16 (1982).
Giustina et al., J. Endocrinol. Invest. 8:19–23 (1985).
Lunetta et al., J. Endocrinol. Invest. 4:185–88 (1981).
MacIntyre, Regulatory Peptides 34:81 (1991).
Passeri et al., G. Clin. Med. 55:362–70 (1973).
Sgambato et al., Acta Diabet. Lat. 18:235–41 (1981).
Starke et al., Diabetologia 20:547–52 (1981).
Stracca et al., Calcitonin 1984; Yamaguchi, Chem. Pharm. Bull. 29:1455–58 (1981).
Yamaguchi, Endocrinol. Japon. 28:643–46 (1981).
Yamaguchi, Endocrinol. Japon. 28:51–57 (1980).
Yamaguchi et al., Chem. Pharm. Bull. 25:2189–94 (1977).
Ziegler et al., Horm. Metab. Res. 4:60 (1972).
Zofkova et al., Exp. Clin. Endocrinol. 89:91–96 (1987).
Zofkova et al., Horm. Metabol. Res. 19:656–60 (1987).
Zofkova, Acta. Univ. Carol. Med. 32:319–25 (1986).
Ferlito et al., Il Farmaco–Ed. Pr. –vol. 37–fasc. 7:239–44 (1982).
Zamrazil et al., Horm. Metab. Res. 13:631–35 (1981).
Yamaguchi et al., Diabetes 39:168–74 (1990).

Primary Examiner—Howard E. Schain
Assistant Examiner—Benet Prickril
Attorney, Agent, or Firm—Lyon & Lyon

[57] ABSTRACT

Methods for treatment of diabetes and other insulin-requiring conditions by administering insulin and a calcitonin with or without amylin, and methods for treatment of hypoglycemic conditions by administering a calcitonin alone or in combination with glucagon and/or an amylin, and related compositions.

17 Claims, 3 Drawing Sheets

METHODS AND COMPOSITIONS FOR TREATMENT OF DIABETES MELLITUS, HYPOGLYCEMIA & OTHER CONDITIONS

RELATED APPLICATIONS

This is a continuation of application Ser. No. 08/129,569 filed on Sept. 29, 1993, now abandoned, which is a divisional of U.S. application Ser. No. 07/774,411, filed Oct. 10, 1991 now U.S. Pat. No. 5,320,008, which is a continuation-in-part of Beaumont et al., U.S. application Ser. No. 07/670,231, filed Mar. 15, 1991, entitled "Receptor-Based Screening Methods for Amylin Agonists and Antagonists" now U.S. Pat. No. 5,264,372, Young et al., which is a continuation-in-part, U.S. application Ser. No. 07/640,478, filed Jan. 10, 1991, entitled "Hyperglycemic Compositions", now U.S. Pat. NO. 5,234,906 and Young et al., U.S. application Ser. No. 07/704,995, filed May 24, 1991, which is a continuation-in-part, entitled "Treatment of Insulin Deficient Mammals" now abandoned, all of which (including drawings) are hereby incorporated by reference.

FIELD OF THE INVENTION

The invention relates to methods and compositions for treatment of diabetes mellitus, and other insulin requiring conditions, as well as hypoglycemia.

BACKGROUND OF THE INVENTION

Diabetes mellitus is a metabolic disorder defined by the presence of chronically elevated levels of blood glucose (hyperglycemia). Insulin-dependent (Type 1) diabetes mellitus ("IDDM") results from an autoimmune-mediated destruction of pancreatic β-cells with consequent loss of insulin production, which results in hyperglycemia. Type 1 diabetics require insulin replacement therapy to ensure survival. Non-insulin-dependent (Type 2) diabetes mellitus ("NIDDM") is initially characterized by hyperglycemia in the presence of higher-than-normal levels of plasma insulin (hyperinsulinemia). In Type 2 diabetes, tissue processes which control carbohydrate metabolism are believed to have decreased sensitivity to insulin. Progression of the Type 2 diabetic state is associated with increasing concentrations of blood glucose, and coupled with a relative decrease in the rate of glucose-induced insulin secretion.

The primary aim of treatment in both forms of diabetes mellitus is the same, namely, the reduction of blood glucose levels to as near normal as possible. Treatment of Type 1 diabetes involves administration of replacement doses of insulin, generally by the parenteral route. In contrast, treatment of Type 2 diabetes frequently does not require administration of insulin. For example, initial therapy of Type 2 diabetes may be based on diet and lifestyle changes augmented by therapy with oral hypoglycemic agents such as a sulfonylurea. Insulin therapy may be required, however, especially in the later stages of the disease, to produce control of hyperglycemia in an attempt to minimize complications of the disease.

Treatment with oral hypoglycemic agents such as a sulfonylurea may lead to hypoglycemic reactions, including coma, four or more hours after meals. These hypoglycemic episodes may last for several days, so that prolonged or repeated glucose administration is required. Such hypoglycemic reactions are unpredictable and may occur after as little as one dose, after several days of treatment, or after months of drug administration. Most hypoglycemic reactions are observed in patients over 50 years of age, and are most likely to occur in patients with impaired hepatic or renal function. Over-dosage of sulfonylurea, or inadequate or irregular food intake may initiate such hypoglycemic reactions. Other drugs can increase the risk of hypoglycemia from sulfonylureas; these include other hypoglycemic agents, sulfonamides, propranolol, salicylates, phenylbutazone, probenecid, dicumarol, chloramphenicol, monoamine oxidase inhibitors, and alcohol.

As with the sulfonylurea agents, hypoglycemia (typically characterized by a blood-glucose level below about 60 mg/dl) is the major adverse effect of insulin therapy. Hypoglycemia is by far the most serious and common adverse reaction to the administration of insulin, and can result in substantial morbidity and even death. Insulin-induced hypoglycemia is experienced at some time by virtually all Type 1 diabetics, and is reported to account for about 3–7% of deaths in patients with Type 1 diabetes. Shafrir, E., et al., in Felig, P., et al, "Endocrinology and Metabolism," pages 1043–1178 (2nd ed. 1987). Although rates of hypoglycemic incidents vary among individuals, patients undergoing conventional insulin therapy suffer an average of about one episode of symptomatic hypoglycemia per week, whereas those practicing intensive insulin therapy suffer about two to three such episodes per week. Thus, over a time frame of forty years of Type 1 diabetes, the average patient can be projected to experience two thousand to four thousand episodes of symptomatic hypoglycemia. Approximately 10% of patients undergoing conventional insulin therapy suffer at least one episode of severe hypoglycemia, i.e., requiring assistance from others, including hyperglycemic treatment such as glucose or glucagon administration, and episodes with seizure or loss of consciousness, in a given year. The yearly incidence of severe hypoglycemic episodes rises to about 25% among patients undergoing intensive therapy. Cryer, P. E., et al., "Hypoglycemia in IDDM," *Diabetes* 38:1193–1198 (1989).

The brain has only an extremely limited ability to store carbohydrate in the form of glycogen, and (except during prolonged starvation) is almost entirely dependent on glucose as its source of energy; thus, it is very sensitive to hypoglycemia. Symptoms of cerebral dysfunction rarely occur until the glucose content of the cerebral arterial blood falls below 60 mg/dl. However, symptoms of hypoglycemia may occur even though the blood-glucose is normal or only minimally reduced, if there has been a rapid fall from a much higher level. Severe or recurrent episodes of hypoglycemia may result in permanent cerebral damage.

Glucagon is widely used clinically in the acute management of severe hypoglycemia complicating insulin replacement therapy of insulin-dependent (type 1) diabetes mellitus. Glucagon is particularly useful in the treatment of insulin-induced hypoglycemia when dextrose (glucose) solution is not available or, for example, when a patient is convulsing or recalcitrant and intravenous glucose cannot be administered. Glucagon is effective in small doses, and no evidence of toxicity has been reported with its use.

When given, glucagon may be administered intravenously, intramuscularly, or subcutaneously, typically in a dose of 1 milligram. Once glucagon is introduced for hypoglycemic coma induced by either insulin or oral hypoglycemic agents, a return to consciousness should be observed within 20 minutes. In any event, intravenous glucose should be administered where possible. Salter, *Common Medical Emergencies*, p. 144 (2nd ed., J. Wright & Sons 1975); *Goodman and Gillman's The Pharmacologic Basis of Therapeutics*, p. 1510–1512 (7th ed. 1985).

SUMMARY OF THE INVENTION

The utility of glucagon in treating hypoglycemia is limited by its inaction or ineffectiveness in patients with depleted liver glycogen stores. *Physician's Desk Reference* 4th Ed., p. 1215. Since glucagon acts on liver glycogen, but not on skeletal muscle glycogen, by converting it to glucose, it has little or no therapeutically useful hyperglycemic effect in patients with depleted liver glycogen, a condition which cannot be determined in the fitting or nonresponsive patient. Thus, in the convulsing, or comatose patient, for example, glucagon treatment will not alleviate hypoglycemia if the patient has no or insufficient liver glycogen to be mobilized. In addition to states of starvation, it is also understood that glucagon is of little or no help in other states in which liver glycogen is depleted, such as adrenal insufficiency or chronic hypoglycemia. Normally, then, intravenous glucose must be given if the patient fails to respond to glucagon. The most common form of childhood hypoglycemia, "ketotic (idiopathic glucagon unresponsive) hypoglycemia" is characterized by the failure of glucagon to raise circulating glucose in the fasting state.

Co-pending application of Young et al., supra, describes the use of glucagon and amylin or its agonists for treating acute hypoglycemia and other hypoglycemic conditions. Amylin was found to increase blood glucose levels even when glucagon had little effect, since it appeared to cause release of metabolic fuel from skeletal muscle stores, rather than liver stores.

This application describes the use of calcitonin, an amylin agonist, alone or in conjunction with glucagon and/or amylin in such treatment. Applicants have discovered, unexpectedly, that teleost (bony fish, e.g., salmon and eel) calcitonins and avian (e.g., chicken) calcitonins have a high affinity for receptors which bind amylin with high affinity. For example, experiments described in Beaumont et al., supra, show that salmon calcitonin and eel calcitonin inhibit the binding of $^{125}$I-r amylin to rat basal forebrain membranes. Of the compounds tested, rat amylin was the most potent inhibitor of $^{125}$I-rat amylin binding to the rat basal forebrain membranes. Salmon and eel calcitonin also potently competed for rat amylin binding to the receptors and were only slightly less potent competitors than rat amylin. Rat calcitonin was a weak competitor.

When tested in a rat soleus muscle insulin antagonism assay, both salmon and eel calcitonins were shown to be potent agonists at amylin receptors in rat skeletal muscle. That is, they both effectively reduced insulin-stimulated incorporation of radioglucose into glycogen in rat skeletal muscle at subnanomolar concentrations. Like amylin, salmon calcitonin stimulates breakdown of glycogen in the isolated soleus muscle of the rat.

Our studies show, for the first time, that calcitonin as well as amylin can modulate muscle glycogen metabolism, and in a dose-dependent manner.

The present invention provides for the administration of a calcitonin for the treatment of a hypoglycemic condition, especially acute hypoglycemia as may be brought on by insulin overdose or sulfonylurea overdose. In particular, the invention provides for co-administration of calcitonin with glucagon (and/or an amylin) for such treatments. The invention also provides for co-administration of calcitonin (with or without an amylin) and insulin in ongoing treatment of diabetes or other insulin-requiring states.

Thus, in a first aspect, the invention features a method for the treatment of a hypoglycemic condition in a mammal, by administering a therapeutically effective amount of a calcitonin, effective to increase blood sugar level in the mammal.

In another aspect, the invention features treatment of diabetes mellitus or other insulin-requiring states by administering a therapeutically effective amount of an insulin and a calcitonin, with or without a therapeutically effective amount of an amylin.

By "therapeutically effective amount" of a calcitonin in the treatment of hypoglycemia is meant an amount that increases blood sugar levels, preferably to above 80 mg/dl. By "therapeutically effective amount" of a calcitonin in the treatment of diabetes mellitus and other insulin-requiring states is an amount sufficient to provide for reduced incidence of insulin overdose or hypoglycemia.

The term "calcitonin" is used above in a manner well known by those in the art (see, Azria, Calcitonins—Physiological and Pharmacological Aspects, pp. 1–31, Springer-Verlag, 1989). For example, the term is meant to include peptides similar to a 32 amino acid peptide isolated from porcine thyroid glands. The hormone is synthesized and secreted by the parafollicular C cells of the thyroid gland in mammals. Calcitonins from several submammalian vertebrates have been sequenced. In these submammalian species, calcitonin is stored in cells located in the ultimobranchial body, which is separated from the thyroid gland. Calcitonins from fish (e.g., salmon and eel), and the closely related chicken calcitonin, are sometimes termed ultimobranchial calcitonins due to their location in ultimobranchial bodies.

In mammals, calcitonin is held to function in the regulation of bone turnover and calcium metabolism. Calcitonin is released from the thyroid by elevated serum calcium levels, and produces actions upon bone and other organs which tend to reduce serum calcium levels. Calcitonin inhibits osteoclast activity and reduces bone resorption, thereby reducing serum calcium levels. Calcitonin also alters calcium, phosphate and electrolyte excretion by the kidney, although this appears to be a minor effect and its physiological significance is not known.

The term is also meant to include peptides or their equivalent having similar amino acid sequences to known calcitonins and having one or more of the known biological activities, in particular, the ability to increase circulating glucose concentration in humans. Such peptides include those referred to as functional equivalents or functional calcitonin fragments, and conservative variants thereof. The calcitonin can be administered by any known route, including nasal administration. See, 2 *BioWorld Today*, Vol. 125, 2, 1991.

While calcitonin has been used clinically for treatment of disorders of calcium metabolism and pain, and its relationship to increased glucose levels in mammals has been the subject of varying reports, its use as an agonist of amylin in the treatment of diabetes or hypoglycemia has not been suggested. See, e.g., Azria et al., "Calcitonins—Physiological and Pharmaclological Aspects," pp.24–25 (Springer-Verlag 1989). Indeed applicants are the first to demonstrate its utility, and the first to suggest its clinical use, for treatment of diabetes and other insulin-requiring states, as well as hypoglycemia.

In preferred embodiments for the treatment of hypoglycemia, the method of the present invention includes the step of identifying a mammal having a hypoglycemic condition, prior to the administering step. The method also includes administering a therapeutically effective amount of a glucagon to the mammal, effective to increase blood sugar level in the mammal, e.g., the amount of calcitonin and glucagon together is sufficient to alleviate said condition, or the amount of calcitonin alone is sufficient to alleviate the condition.

In other preferred embodiments, the method includes the step of administering a therapeutically effective amount of an amylin effective to increase, or aid in increasing, blood sugar level in the mammal. The hypoglycemic condition to be treated may exist in a diabetic mammal, e.g., a human who suffers from diabetes mellitus, Type 1 or Type 2.

The term "amylin" is used in this application as defined by Young et al., supra. For example, it includes the peptide hormone referred to as amylin which is synthesized and secreted from the beta cells of the pancreas. Amylin functions along with insulin, which is stored and released from the same pancreatic beta cells, to regulate fuel metabolism. Amylin acts through receptors located in skeletal muscle to increase glycogen turnover in this tissue, believed to result in an increased return to the bloodstream of lactate, which is a major precursor of hepatic gluconeogenesis. Amylin cosecretion with insulin after meals therefore results in restoration of hepatic glycogen content and limits the potential which would otherwise exist for insulin to induce hypoglycemia. Administration of amylin to anesthetized rats produces large increases in blood lactate levels, presumably through a direct effect upon skeletal muscle glycogen breakdown and glycolysis. Increased blood lactate content is followed rapidly by increased blood glucose levels, believed to result from provision of gluconeogenic precursors in the form of lactate to the liver. These physiological and pharmacological effects of amylin form the basis for its therapeutic indications in treatment of Type 1 diabetes and hypoglycemia.

The term "glucagon" is an art-recognized term, as discussed above. This term also includes peptide fragments having glucagon-like activity as discussed above.

By "identifying" is meant to include noting the symptoms or characteristics of hypoglycemia, e.g., those discussed above. Such symptoms are well known in the art. It also includes chemical or biochemical assays which indicate such conditions, or their equivalent.

In other related aspects, the invention features a composition including a therapeutically effective amount of a calcitonin and an insulin admixed in a form suitable for therapeutic administration; and a composition including a therapeutically effective amount of a calcitonin and glucagon admixed in a form suitable for therapeutic administration.

These compositions are useful in the above methods, the former composition for chronic treatment of diabetes.

By "insulin" is meant a polypeptide or its equivalent useful in regulation of blood glucose levels. A general description of such insulins is provided in *Goodman and Gilman's, The Pharmacological Basis of Therapeutics*, 8th ed., Maxmillan Pub. Co. (1990). Such insulins can be fast acting, intermediate acting, or long acting. Id. at 1502. Various derivatives of insulin exist and are useful in this invention. See e.g., U.S. Pat. Nos. 5,049,547, 5,028,587, 5,028,586, 5,016,643. Insulin peptides are also useful (see e.g., U.S. Pat. No. 5,008,241), as are analogues (see e.g., U.S. Pat. Nos. 4,992,417 and 4,992,418). Such insulin can be administered by any standard route, including nasal administration, see e.g., U.S. Pat. Nos. 4,988,512 and 4,985, 242, and 2 *BioWorld Today*, No. 125, 1, 1991.

In preferred embodiments, the effective amount of the calcitonin is between 0.001 mg and 0.1 mg per kg of body weight per day; the calcitonin is selected from the group consisting of calcitonin of avian origin (including chicken calcitonin) and teleost origin (including eel calcitonin and salmon calcitonin); the ratio of the therapeutically effective amount of the calcitonin and the therapeutically effective amount of the insulin will normally range from about 2:1 to about 1:100, preferably from about 1:1 to about 1:20 and, more preferably, will be in a ratio of about 1:10; the ratio of the therapeutically effective amount of the calcitonin and the therapeutically effective amount of the glucagon is from about 1:1 to about 1:10, and is preferably about 1:1; and the compositions may further include an amylin.

BRIEF DESCRIPTION OF THE DRAWINGS

The drawings will first briefly be described.
Drawing

DETAILED DESCRIPTION OF THE INVENTION

Calcitonin

Calcitonins are generally described above. Those useful in this invention are amylin agonists and may be identified in numerous ways, e.g., by a receptor assay. The affinity of various calcitonins for amylin receptors can be measured in the amylin receptor assay described by Beaumont et al., supra. Unexpectedly, the ultimobranchial calcitonins were found to have very high affinity for these receptors, similar to that of amylin itself. Concentrations of peptide producing 50% inhibition ($IC_{50}$) of binding of radiolabeled amylin to amylin receptors are shown in Table 1. Rat and human calcitonin have very low affinities for amylin receptors, since concentrations as high as 1 micromolar did not produce 50% inhibition of binding. The other calcitonins are useful in this invention. Generally, a calcitonin having an $IC_{50}$ less than 1.0 nM, preferably less than 0.1 nM, is useful in this invention.

Similarly, the ultimobranchial calcitonins are potent inhibitors of insulin-stimulated glycogen synthesis and stimulators of glycogen breakdown in isolated rat soleus muscle (see Table 1), and thus useful in the invention. Preferably they have an $EC_{50}$ of less than 5 nM and, more preferably, less than 2 nM in such an assay.

TABLE 1

| Peptide | Receptor Binding ($IC_{50}$, nM) | Soleus Muscle ($EC_{50}$, nM) |
| --- | --- | --- |
| Human amylin | 0.05 | 1.6 |
| Chicken calcitonin | 0.03 | 0.7 |
| Salmon calcitonin | 0.07 | 0.4 |
| Eel calcitonin | 0.09 | 0.4 |
| 1,7-Asn-eel calcitonin | 0.05 | 0.3 |

These results indicate that ultimobranchial calcitonins have high affinity for amylin receptors and are potent agonists in assays of amylin receptor-mediated functional effects.

Figure 1:
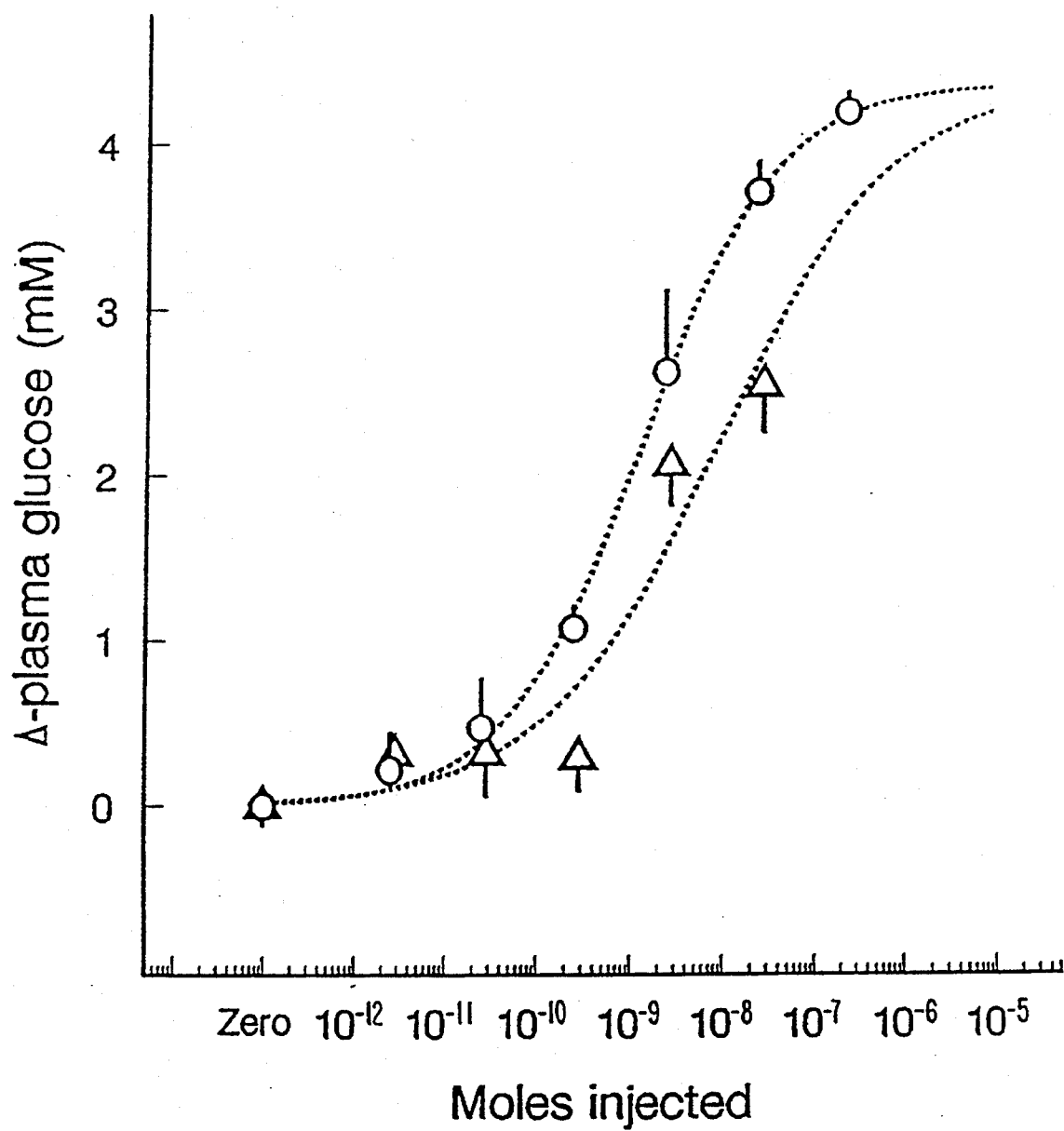
FIG. 1 is a graphical representation of dose responses for changes in plasma glucose following amylin or calcitonin. Adult HSD male rats were fasted for about 20 hours and lightly anesthetized. They were then administered a single intravenous bolus injection of different doses of rat amylin (○), or salmon calcitonin (△) plotted as molar doses. The increments in plasma glucose over the control (saline) response were measured 30 minutes post-injection. Symbols are means ± s.e.m.
Figure 2:
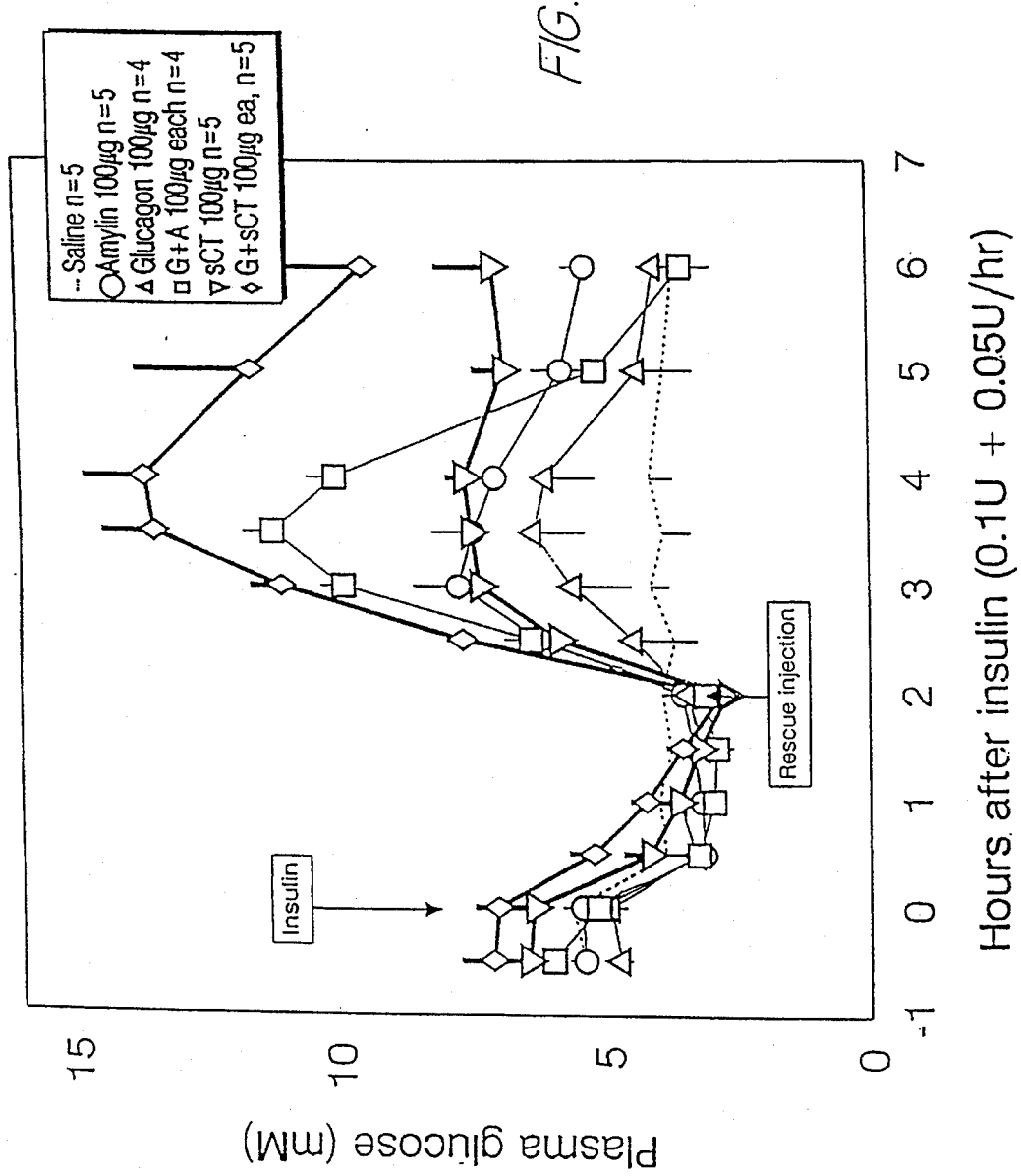
FIG. 2 is a graphical representation of plasma glucose response from insulin-induced hypoglycemia. Rats fasted about 20 hours were anesthetized and infused with insulin (100 mU+50 mU/hr) for 2 hours before and then for a further 4 hours after bolus intravenous injection of saline ( - - - ;n=5); amylin 100 μg (○;n=5); glucagon 100 μg (△;n=4); glucagon 50 μg+ amylin 50 μg (□;n=4); salmon calcitonin 100 μg (▽,n=5); or calcitonin 100 μg+glucagon 100 μg (◇;n=5). Symbols are means ± s.e.m. Using the integrated increment in plasma glucose for the 2 hours after "rescue" injection (trapezoidal integral), there was a significant difference within the five "rescue" treatments (ANOVA, P<0.001).
Figure 3:
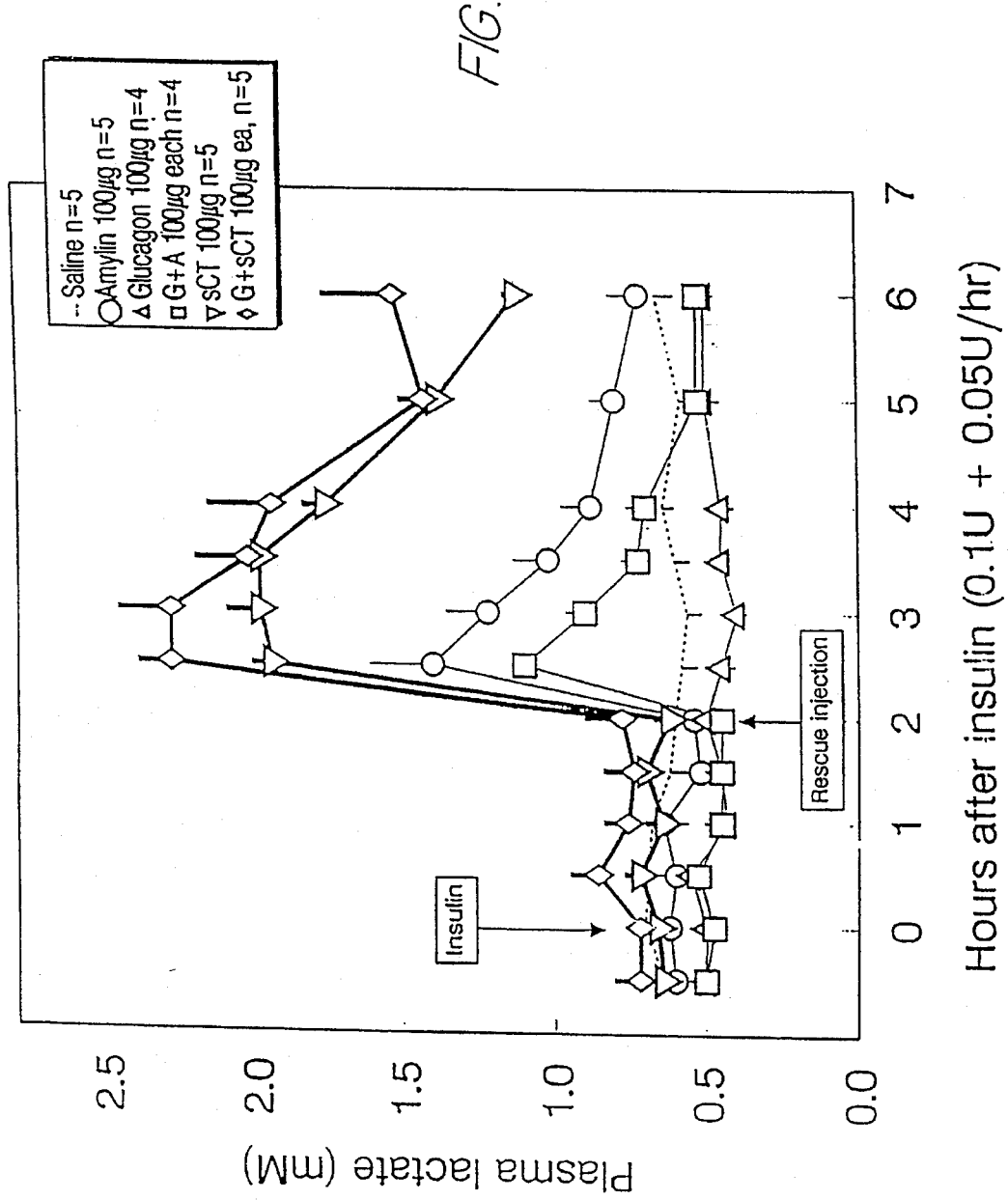
FIG. 3 is a plasma lactate response from insulin-induced hypoglycemia. The symbols have the same assignments and meanings as in FIG. 2.

The utility of these calcitonins was further demonstrated as follows. Following intravenous administration in anesthetized rats, salmon and eel calcitonin had potent amylin agonist-like activity. These peptides produced a rapid hyperlactemia followed by hyperglycemia. As shown in FIGS. 2 and 3, these acute effects are similar to those produced by administration of amylin. Ultimobranchial calcitonins are potent in vivo and in vitro amylin agonists, and their usefulness has been demonstrated herein for clinical situations such as, e.g., diabetes and hypoglycemia, in which amylin activity is deficient or would be usefully supplemented.

The following example is illustrative, but not limiting of the methods for determining the hyperglycemic utility of various compositions (including a calcitonin) and methods of the present invention. Other suitable compounds that may be modified or adapted for use are also appropriate and are within the spirit and scope of the invention. Further examples are provided in those co-pending applications noted above and incorporated by reference. These examples are not repeated herein and are not essential to the invention.

EXAMPLE 1

In vivo treatment of rats

In vivo potency of rat amylin or salmon calcitonin at doses ranging from 0.01 μg to 1000 μg (about 7 pmol/kg–700 nmol/kg; in a 10-fold dilution series) was determined in fasted lightly anesthetized rats given single intravenous bolus injections. Control animals received an equal volume of saline. The treatment resulted in rapid increases in plasma levels of glucose.

Adult male Harlan Sprague Dawley rats were housed at 22.7±0.8° C. in a 12:12 hour light:dark cycle (experiments being performed during the light cycle), and were fed and watered ad libitum (Diet LM-485, Teklad, Madison, Wis.). All the animals were fasted for approximately 20 hours before experimentation.

Anesthesia was induced with 5% halothane, maintained at 2% during surgery and at 0.7–1% thereafter. Tracheotomy and cannulation of the right femoral artery and saphenous vein were performed. The arterial line, perfused with heparinized saline (2 U/mL) at 3 mL/hour, was used for blood sampling. The venous line was used for bolus injection. Colonic temperature was measured and controlled using a thermistor probe/controller (Model 73A, YSI, Yellow Springs, Ohio) and a heated operating table.

After a 2-hour equilibration period, animals were injected with a 100 μL bolus of saline containing an amount of freshly dissolved rat amylin (Lot No. ZG485, Bachem Inc., Torrance, Calif.) or salmon calcitonin (Lot No. QG407, Bachem).

Since the activity of synthesized amylins may vary, the bioactivity of the amylin used in this study was first verified in vitro in isolated soleus muscle ($EC_{50}=6.7\pm1.5$ nM). Plasma glucose was measured at −30, −15, 0, 30, 60, 90 and 120 min. post-injection. Changes in plasma glucose at 30 minutes over those observed in saline injected controls constitute the responses reported in the present study.

Arterial blood was collected into heparinized capillary tubes and the separated plasma analyzed immediately for glucose using immobilized enzyme chemistries (glucose oxidase, Analyzer model 2300-STAT, YSI, Yellow Springs, Ohio).

Both ligands, amylin and calcitonin, produced dose dependent increases in plasma glucose. The same $ED_{50}$ was obtained whether glucose increment at 30 minutes, or the peak increment (60–90 minutes) was used; the response at 30 minutes is therefore used here.

The Figure shows the increase in plasma glucose as a function of intravenous dose of rat amylin and salmon calcitonin. The $ED_{50}$'s for the response, detailed in Table 2, were comparable (within about half a log unit), with amylin having somewhat greater hyperglycemic potency than calcitonin. The potency ratio for amylin:salmon calcitonin was 6.78.

TABLE 2

| | Dose response characteristics ($ED_{50}$) | | |
| --- | --- | --- | --- |
| Peptide | Response | Magnitude | $ED_{50}$ |
| rAmylin | Glucose (30 min) | +4.35 mM | 1.34(3.93) |
| sCalcitonin | Glucose (30 min) | +4.35 mM | 9.21(25.9) |

The present study demonstrates that amylin and calcitonin both increase plasma glucose in a similar and dose-dependent manner.

EXAMPLE 2

In vivo treatment of hypoglycemic rats

Male Harlan Sprague Dawley rats were housed at 22.7°±0.8° C. in a 12:12 hour light:dark cycle (experiments being performed during the light cycle) and fed and watered ad libitum (Diet LM-485, Teklad, Madison, Wis.). Animals were deprived of food for about 20 hours prior to experimentation.

Anesthesia was induced with 5% halothane, maintained at 2% during surgery and at 0.8–1% during metabolic recordings. Tracheotomy and cannulation of the right femoral artery and saphenous vein were performed. The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. All chronically infused agents were added to this infusate. The venous line was used for acute (bolus) injections. A 4-limb ECG was monitored via an ECG/biotach amplifier (Model 13-4615-65A, Gould, Cleveland, Ohio) and heart rate derived. Colonic temperature was measured using a thermistor probe and controller (Model 73A, YSI, Yellow Springs, Ohio) which provided closed-loop control of core temperature by switching a heated operating table. Signals for heart rate, mean arterial pressure and colonic temperature were periodically sampled and stored with 12-bit precision at 1 Hz using a computerized data acquisition system (DT2801A A/D converters, DataTranslation, Marlboro, Mass.; AST Premium 386 computer, AST Research, Irvine, Calif.; Labtech Notebook software, Laboratory Technologies Corp, Wilmington, Mass.).

Due to potential variations in biological activity of commercially available amylin preparations, synthetic rat amylin (lot #ZG485, Bachem, Torrance, Calif.) was first tested for bioactivity using the soleus muscle based assay ($EC_{50}$= 6.7±1.5 nM). The glucagon preparation used was a therapeutic formulation (Glucagon for injection USP, Eli Lilly and Company, Indianapolis, Ind.; lot #4MC51D, containing glucagon 1 mg, lactose 49 mg constituted into 1 mL aqueous solution of 1.6% glycerin and 0.2% phenol). Salmon calcitonin (synthetic cyclic) was obtained from Bachem, Torrance, Calif. (lot#QG407).

Fasted Harlan Sprague Dawley rats, prepared as above, were administered a 100 mU/50 mU/hr (710 nmol/355 nmol/hr) primed/continuous infusion of recombinant human insulin (Humulin-R, Eli Lilly, Indianapolis, Ind.). Peptides were otherwise as specified above. After 2 hours infusion when steady-state hypoglycemia had been attained (3.35±0.17 mM), the animals received a 0.1 mL intravenous bolus containing one of the following:

1. Saline (0.15M); animals were fasted 20.8±0.5 hr.
2. Glucagon, 100 μg (28.7 nmol); animals were fasted 19.9±0.7 hr.
3. Amylin (rat synthetic), 100 μg (25.5 nmol); animals were fasted 20.9±0.6 hr.
4. Glucagon, 50 μg+amylin, 50 μg; animals were fasted 20.6±0.2 hr.
5. Glucagon, 200 μg.
6. Glucagon, 100 μg+amylin, 100 μg; animals were fasted 21.3±0.1 hr.
7. Calcitonin (salmon synthetic), 100 μg (29.2 nmol); animals were fasted 21.1±0.2 hr.
8. Calcitonin, 100 μg+glucagon, 100 μg; animals were fasted 21.1±0.2 hr.

For convenience, injections of amylin/calcitonin and/or glucagon are collectively referred to as "rescue" injections in the text and in FIGS. 2 and 3.

Arterial samples were drawn at 0.5 hr intervals into heparinized capillaries and the separated plasma analyzed immediately for glucose and lactate using immobilized enzyme chemistries (glucose oxidase, L-lactate oxidase, Analyzer model 2300-STAT, YSI, Yellow Springs, Ohio). Plasma was collected for insulin measurement every 2 hours. Insulin was determined by radioimmunoassay (Micromedic human insulin RIA kit, ICN Biomedicals, Horsham, Pa.) with a sensitivity of 6 pM and a cross-reactivity to rat insulin of 89.5%.

Pairwise statistical analyses used Student's t-test routines (pooled variances method) contained in the Statistics (STATS) module of the SYSTAT system (Wilkinson, SYSTAT: The system for statistics, Systat Inc., Evanston, Ill.). General effects were testing using the one-way analysis of variance contained within the Multivariate General Linear Hypothesis (MGLH) module of the SYSTAT system. All results are reported as means±s.e.m. and, unless stated otherwise, $P<0.05$ is used as the level of significance.

Referring to FIG. 2, the plasma glucose response in fasted rats subjected to insulin-induced hypoglycemia following administration of saline, amylin, glucagon, calcitonin, and the glucagon+amylin and glucagon+calcitonin combinations is shown. The mean plasma insulin before infusion was 114±17 pM, increasing ~11-fold to 1304±303 pM by 2 hours after infusion. There were no differences in basal or attained insulin concentrations between the different treatment groups (P=0.13,0.79 respectively, ANOVA).

As can be seen in FIG. 2, injection of amylin, glucagon, calcitonin, or glucagon+amylin or glucagon+calcitonin combined evoked a substantial increase in plasma glucose ($P<0.05$ for each treatment vs saline, 2-hour integrated response) which rose to a level equal to or greater than that observed before insulin infusion. Amylin alone, calcitonin alone, or either in combination with glucagon, increased plasma glucose above the pre-insulin infusion level for longer periods and to a greater extent than did glucagon alone. Under the present experimental circumstances, 100 μg (~90 nmol/kg) of glucagon appeared to be maximally effective, and from studies using a similar preparation (Wang et al., 40 *Diabetes*, 241A, 1991), the 100 μg dose of amylin used in the present experiments is likely to have been around 85% maximal. From dose-response studies in an experimental preparation similar to that used (data not shown) it is likely that the response to 100 μg glucagon was about 70% maximal. While little further glucose response may have been expected by increasing amylin or glucagon doses alone, the responses to glucagon and amylin combined were at least additive; 50 μg of each glucagon and amylin gave a response 1.5-fold (P=0.2)larger than the same mass (100 μg) amylin and 2.26-fold larger than the same mass (100 μg) of glucagon ($P<0.05$). 100 μg of each, glucagon and amylin, given together resulted in peak and integrated responses at least as great as the sum of effects of separate doses (2.88 cf. 1.00+1.51 times the glucagon effect, see Table 3). Salmon calcitonin alone resulted in significant hyperglycemia ($P<0.001$ vs saline) that was greater than that produced by 100 μg glucagon ($P<0.01$), and equivalent to that produced by amylin alone (P=0.32). Glucagon (100 μg) added to salmon calcitonin resulted in a hyperglycemic response greater than the sum of the individual responses of calcitonin or glucagon (3.68 cf. 1.00+1.85). That is, there was a synergy.

TABLE 3

Relative effectiveness of hormones and hormone combinations in elevating plasma glucose concentration: referenced to 100 μg glucagon

| Hormone/combination<br>glucagon = 1 | Δglucose<br>mM. hrs | Effectiveness<br>100 μg<br>saline = 0 |
| --- | --- | --- |
| Saline | 0.17±1.11 | 0.00 |
| Glucagon 100 μg | 3.90±0.86[a] | 1.00 |
| Amylin 100 μg | 5.82±1.06[b] | 1.51 |
| Amylin 50 μg/Glucagon 50 μg | 8.61±1.31[bc] | 2.26 |
| Glucagon 200 μg | 2.43±0.62[a] | 0.61 |
| Amylin 100 μg/Glucagon 100 μg | 10.93±0.89[bd] | 2.88 |
| Calcitonin 100 μg | 7.06±0.47[b] | 1.85 |
| Calcitonin 100 μg/<br>Glucagon 100 μg | 13.91±1.04[bd] | 3.68 |

[a]$P < 0.05$ vs saline, [b]$P < 0.01$ vs saline, [c]$P < 0.05$ vs 100 μg glucagon, [d]$P < 0.01$ vs 100 μg glucagon. Effectiveness, measured as the integral of the increase in glucose for 2 hours after the "rescue" injection, is indicated relative to saline or 100 μg glucagon (saline = 0, glucagon = 1).

FIG. 3 shows the lactate response to intravenous injections of saline, amylin, glucagon, calcitonin and amylin+glucagon and calcitonin+glucagon combinations as described above. Insulin infusion did not significantly change plasma lactate. Glucagon did not affect plasma lactate concentration. Amylin, calcitonin and both amylin+glucagon and calcitonin+glucagon combinations caused rapid elevations of plasma lactate, consistent with the mechanisms of action of amylin (Young et al., 291 *FEBS Letters* 101–104, 1991).

The results demonstrate that, whereas glucagon acts mainly via activation of hepatic glycogenolysis and gluconeogenesis, amylin works mainly via activation of muscle glycogenolysis and subsequent peripheral lactate release. Both groups of hormones can raise plasma glucose levels; glucagon is more effective in the fed animal where there are substantial hepatic glycogen stores; amylin and calcitonin are more effective hyperglycemic agents in fasted animals.

Salmon calcitonin has been reported to elevate plasma glucose (Evans et al., 1 *Lancet* 280, 1978), although the mechanism by which this happened remained obscure; the principal effects were believed by some workers (Passariello et al., 53 *J. Clin. Endocrinol. Metab.* 318–23, 1981) to be pancreatic mediated through inhibition of insulin secretion; like amylin (Silvestre et al., 31 *Regulatory Peptides* 23–31, 1990), calcitonin inhibits both glucose-mediated and arginine-mediated insulin secretion but not arginine-stimulated glucagon release (Passariello, 53 *J. Clin. Endocrinol. Metab.* 318–23, 1981). We have determined that the principal mechanism by which salmon calcitonin raises blood glucose is equivalent to the peripheral effect of amylin. In vitro, in the isolated soleus muscle, salmon calcitonin inhibits incorporation of radioglucose into glycogen by activating glycogenolysis. That is, as with amylin, calcitonin is held to cause hyperglycemia by releasing lactate from peripherally stored glycogen (principally in muscle) which is then converted by gluconeogenesis into glucose. The concordance of the pancreatic effects of amylin and salmon calcitonin referred to above support the concept that they act at the same receptor. The hyperlactemia produced by both amylin and salmon calcitonin cannot be explained by the pancreatic effects of these hormones. Moreover, it is our determination that not only is the hyperlactemia a consequence of amylin or calcitonin-induced glycogenolysis, but that it is necessary for the ensuing hyperglycemia; the hyperglycemic effects can be reproduced by an hyperlactemia characteristic of that described to result from the glycogenolytic effect of amylin (Young et al., 291 FEBS *Letters* 101–104, 1991).

The comparison of glucagon, amylin and calcitonin responses supports the clinical application of the herein described calcitonins in treatment of diabetes mellitus and other insulin-requiring states, as well as hypoglycemia. For hypoglycemia, established therapies are glucose and/or glucagon (Salter, *Common Medical Emergencies:* 2nd Edition, John Wright and Sons Ltd. Briston, p. 142). Glucagon's clinical utility is well recognized to be limited by availability of mobilizable liver glycogen (E. R. (Publisher) Barnhart (1990) *Physicians Desk Reference*: Edition 44, Medical Economics Company Inc., Oradell, N.J. p. 125. In other clinical situations, such as ketotic (idiopathic glucagon-unresponsive) hypoglycemia (Rosenbloom et al., 47 *Arch. Dis, Child.* 924–6, 1972), it may be ineffective. Since amylin and salmon calcitonin are more effective than glucagon in eliciting an increase in blood glucose in the glycogen depleted state and are at least additive with glucagon in reversing hypoglycemia, they should offer an important alternative or adjunct therapy to glucagon in this condition. The use of calcitonins in connection with insulin therapy in diabetes mellitus (both Type 1 and Type 2) and other insulin-requiring states, is also substantiated by the above in vivo test results.

Compositions

Compositions or products according to the invention may conveniently be provided in the form of solutions suitable for parenteral (including intravenous, intramuscular and subcutaneous) or nasal or oral administration. In many cases, it will be convenient to provide an insulin or glucagon and a calcitonin in a single composition or solution for administration together. In other cases, it may be more advantageous to administer insulin and calcitonin separately. A suitable administration regime may best be determined by a doctor for each patient individually. Suitable formulations including insulin are known in the art.

The stability of calcitonin preparations may be increased at neutral pH. Neutral preparations of calcitonin may be mixed with appropriate preparations of insulin, resulting in increased clinical utility. A form of repository or "depot" slow release preparation may also be used so that therapeutically effective amounts of the preparation are delivered into the bloodstream over many hours or days following transdermal injection.

Since the products of the invention are amphoteric they may be utilized as free bases, as acid addition salts or as metal salts. The salts must, of course, be pharmaceutically acceptable, and these will include metal salts, particularly alkali and alkaline earth metal salts, e,g., potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The products of the invention will normally be provided as parenteral compositions for injection or infusion. They can, for example, be suspended in an inert oil, suitably a vegetable oil such as sesame, peanut, or olive oil. Alternatively, they can be suspended in an aqueous isotonic buffer solution at a pH of about 5.6 to 7.4. Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkali polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of insulin and/or glucagon and/or amylin and/or a calcitonin which will be effective in one or multiple doses to control or reestablish blood sugar at the selected level. As will be recognized by those in the field, an effective amount of therapeutic agent will vary with many factors including the age and weight of the patient, the patient's physical condition, the blood sugar level to be obtained, and other factor. Typical dosage units for treatment of diabetes mellitus will contain from about 0.1 to 1 mg of a calcitonin and about 0.5 to about 10 mg of an insulin. Typical dosage units for the treatment of hypoglycemia will contain about 0.5 to 1.0 mg of a calcitonin and the art recognized quantity, or less, of a glucagon.

Methods

As defined above, compositions useful in the invention are formulated by standard procedure. These compositions are also administered by standard procedure. Suitable doses are readily determined by those in the art, examples of which are provided above.

Other embodiments are within the following claims.

We claim:

1. A composition comprising a therapeutically effective amount of a calcitonin and a glucagon admixed in a form suitable for therapeutical administration.

2. The composition of claim 1 wherein the effective amount of calcitonin is about 0.5 mg to about 1.0 mg.

3. The composition of claim 1 wherein said calcitonin is selected from the group consisting of calcitonins of avian origin and teleost origin.

4. The composition of claim 1 wherein said calcitonin is chicken calcitonin.

5. The composition of claim 1 wherein the calcitonin is selected from the group consisting of eel calcitonin and salmon calcitonin.

6. The composition of claim 1 wherein the ratio of the therapeutically effective amount of the calcitonin and the therapeutically effective amount of the glucagon is from about 1:1 to about 1:20.

7. The composition of claim 6 wherein said ratio is about 1:1.

8. The composition of claim 1 further comprising an amylin.

9. A method for the treatment of a hypoglycemic condition in a mammal comprising the co-administration to said mammal of therapeutically effective amounts of a calcitonin and a glucagon.

10. The method of claim 9, comprising the step of identifying a mammal having said hypoglycemic condition prior to said administering step.

11. The method of claim 9 or 10 further comprising the step of administering a therapeutically effective amount of a glucagon to said mammal, effective to increase blood sugar level in said mammal.

12. A method of claim 9 wherein said condition exists in a diabetic mammal.

13. The method of claim 12 wherein said mammal is a human who suffers from diabetes mellitus.

14. The method of claim 13 wherein said mammal suffers from diabetes mellitus Type 1.

15. The method of claim 13 wherein said mammal suffers from diabetes mellitus Type 2.

16. A method of claim 9 further comprising administration to said mammal of a therapeutically effective amount of an amylin.

17. The method of claim 11 further comprising the step of administering a therapeutically effective amount of an amylin effective to increase blood sugar level in said mammal.

* * * * *